United States Patent

Ura

[11] Patent Number: 5,941,706
[45] Date of Patent: Aug. 24, 1999

[54] VARIABLE DEPTH MEDICAL DRILL AND METHOD OF MAKING THE SAME

[76] Inventor: Robert S. Ura, 1125 Marine J1R, North Palm Beach, Fla. 33408

[21] Appl. No.: 09/112,600

[22] Filed: Jul. 9, 1998

Related U.S. Application Data

[60] Provisional application No. 60/062,838, Oct. 20, 1997.

[51] Int. Cl.⁶ .............................. A61C 3/02; A61B 17/00

[52] U.S. Cl. .............................. 433/165; 433/72; 606/80

[58] Field of Search ..................................... 433/165, 102, 433/72, 75, 141; 606/80; 408/16; 40/913

[56] References Cited

U.S. PATENT DOCUMENTS

| | | | |
|---|---|---|---|
| 4,904,130 | 2/1990 | Gorman | 408/16 |
| 4,904,185 | 2/1990 | McSpadden | 433/102 |
| 5,087,201 | 2/1992 | Mondani et al. | 433/174 |
| 5,423,677 | 6/1995 | Brattesani | 433/72 |
| 5,429,504 | 7/1995 | Peltier et al. | 433/165 |
| 5,569,035 | 10/1996 | Balfour et al. | 433/165 |
| 5,741,267 | 4/1998 | Jorneus et al. | 433/165 |
| 5,791,902 | 8/1998 | Lauks | 433/165 |

*Primary Examiner*—John J. Wilson
*Assistant Examiner*—Patrick A. Hilsmier

[57] ABSTRACT

A medical or dental drill bit with one or more colored bands to indicate the drilling depth. The colored bands include groove portions filled with a color material. The invention also relates to a method of making such a drill bit.

20 Claims, 3 Drawing Sheets

VARIABLE DEPTH MEDICAL DRILL AND METHOD OF MAKING THE SAME

This application claims the benefit of Provisional Application Ser. No. 60/062,838 filed Oct. 20, 1997.

BACKGROUND OF THE INVENTION

1. Field of the Invention

The present invention relates generally to a medical drill or drill bit, and more particularly to a variable depth medical drill or drill bit having particular applicability as a dental implant drill with improved means for indicating drill depth. The invention also relates to a method of making the above medical drill bit.

2. Description of the Prior Art

In the medical field generally, and in the dental field specifically, drills or drill bits are provided for drilling holes of a specific size and depth in body tissue such as bone or a tooth to a specified depth. For example, a preliminary step in the installation or placement of a dental implant involves drilling a hole in the tooth or tooth root to a specified depth. A dental implant can then be installed into the hole. Accuracy in the depth of the hole is important for a dental implant. If the hole is too shallow, the implant or implant with cover screw will extend above the bone, while if the hole is too deep, the implant will sit below the bone or a pocket will exist at the bottom of the implant. More importantly, inaccurate drill depth can damage vital structures such as nerves and blood vessels. In addition, ultimate success of the implant can be jeopardized. Because of this various drills and techniques have been developed to assist the dentist or other operator in determining the depth of the hole being drilled.

One available drill is a twist drill with spiral flutes extending up the entire length of the drill portion for drawing bone chips and other debris away from the drill tip. Such drills are provided with a plurality of relatively narrow depth indicating rings. These rings are formed by laser etching and are generally black or gray. By drilling a hole to a selected ring, the dentist is able to determine the depth of the hole being drilled. One limitation of this particular drill is the absence of contrast between the laser-etched ring, which is generally black or gray, and the silver color of the stainless steel drill. A second limitation is the absence of any differentiation between the plurality of rings. Thus, it is necessary for the dentist to count the rings as he or she is drilling so that the correct depth is achieved. In some instances, it may be necessary for the dentist to withdraw the drill to recount the rings to make sure that the proper depth of hole is drilled. A third limitation is that the lines tend to wear off with use.

Another drill currently available for use in drilling holes for dental implants is a conventional spade drill having a vertical flute extending up the length of the drill for removing bone and other debris from the cutting tip. Such drill includes a plurality of spaced grooves along the body of the drill to indicate the depths of the hole being drilled. This drill suffers from many of the same limitations as the twist drill described above. First, the grooves in the exterior surface of the drill are often difficult to see because they are the same color as the remainder of the drill. This is particularly true inside the mouth during operation when bone and other debris are being removed. Secondly, there is no differentiation between the plurality of grooves or between adjacent grooves, thus, it is difficult for the dentist to determine the depth of the hole without counting and keeping track of the number of grooves or rings during the drilling process. Thus, similar to the twist drill described above, it is often necessary for the dentist to withdraw the drill from the hole during the drilling process to recheck the particular ring which defines the desired depth.

A further drill structure comprises a twist drill with spirally extending flutes and a plurality of wider laser etched bands to improve their visibility. The width of these bands is such that the bottom edge of the band indicates a first depth, while the top edge indicates a second depth. Although this structure attempts to address the problem of depth marking visibility by making the bands wider, and thus more visible, the bands are still in the same color family as the stainless steel drill tend to wear off with use and also do not differentiate between different depth markings.

Accordingly, there is a need in the art for an improved medical drill, and particularly a dental implant drill, which provides an improved means for indicating the particular depth of the drilled hole and for clearly distinguishing between the markings for holes of different depths.

SUMMARY OF THE INVENTION

In contrast to the prior art, the present invention provides a variable depth medical drill or drill bit, and more specifically a variable depth dental drill or drill bit, having an improved depth determination system. The depth determination system of the present invention overcomes the limitations of the prior art to provide drill depth indications which are clear and easily visible to the user and which easily and readily distinguish different depth indications from one another and do not wear off with use.

More specifically, the present invention relates to a dental drill for drilling holes of specific diameter and depth for installation of dental implants. The drill of the present invention is comprised of an elongated drill shaft with a cutting end at one end, a handpiece attachment end at the opposite end and a plurality of colored bands or rings of contrasting color to the drill bit and of contrasting color to each other. These colored bands or rings are provided in the working portion of the drill bit to indicate different depths. In the preferred embodiment, a plurality of grooves or recesses extend around the shaft at defined locations to function as an indication of the particular depth of the hole being drilled. These grooves are filled with contrasting color materials to not only improve the visibility of the grooves as the drill is spinning, but to also enable the user to visually distinguish between grooves associated with different depths. Also, these color lines will not wear off with use.

In the preferred embodiment, the plurality of color-filled grooves or colored bands extend circumferentially around the drill so that when it is spinning the colored material can be easily seen. Preferably, each groove is provided with a negative draft to cause the colored material positioned within the groove to be more securely retained therein and to prevent dislodgement during operation. The preferred embodiment also contemplates that the colored material in the groove will substantially fill the groove; however, it is possible for a relatively thin layer of colored material to be positioned in the groove or applied to a surface portion of the groove.

A further feature of the present invention relates to an improved structure for a twist drill. A conventional twist drill includes a spiral flute extending the entire length of the drill portion. This leaves little area for any depth marking. Thus, in the prior art twist drills described above, the bands are laser-etched not only on the exterior structure, but in the flutes as well. In accordance with the present invention, a preferred embodiment of the dental drill includes a twist drill tip and a generally vertical or axially extending material removal flute to remove bone and other debris during the drilling process. With the structure of the present invention, the exterior surface area or circumferential dimension of the drill at the groove can be significantly increased to provide circumferentially longer bands of color at each grove. This in turn results in improved visibility.

The present invention also relates to a method of making a medical or dental drill of the type described above. Specifically, the method includes providing a blank drill shaft with a drill cutting tip, and performing a number of machining steps to provide a drill of desired diameter and then providing a plurality of colored bands or rings on the drill shaft in the working area of the bit to indicate variable depths. Preferably, the drill bit is provided with a plurality of depth indicting grooves around the circumference of the drill blank and an axially extending flute. The grooves are then filled with colored material of contrasting colors to form the depth indicating bands or rings.

Accordingly, it is an object of the present invention to provide a medical drill with improved depth indication means.

Another object of the present invention is to provide an improved medical drill with depth indication means which improves the visibility of depth markings and which also distinguishes depth markings of different depths from one another.

A further object of the present invention is to provide an improved dental drill for use in drilling holes to facilitate installation of dental implants and the like and which provides improved depth indicator visibility and a differentiation between indicators for different depths.

Another object of the present invention is to provide an improved variable depth dental drill having depth indicators of contrasting colors.

A still further object of the present invention is to provide a method for manufacturing the medical or dental drill described above.

Yet another object of the present invention is to provide a drill where the markings do not become worn away with use.

These and other objects of the present invention become apparent with reference to the drawings and the description of the preferred embodiment.

DESCRIPTION OF THE PREFERRED EMBODIMENT

The present invention relates to an improved, variable depth drill intended primarily for use in medical and dental applications to drill holes in bone or tooth material of a specific size and to a specified depth. The preferred embodiment, however, will be described with respect to a dental implant drill designed for use primarily in drilling holes of specified size and depth in teeth or teeth bones or roots for the placement of dental implants.

Figure 1:
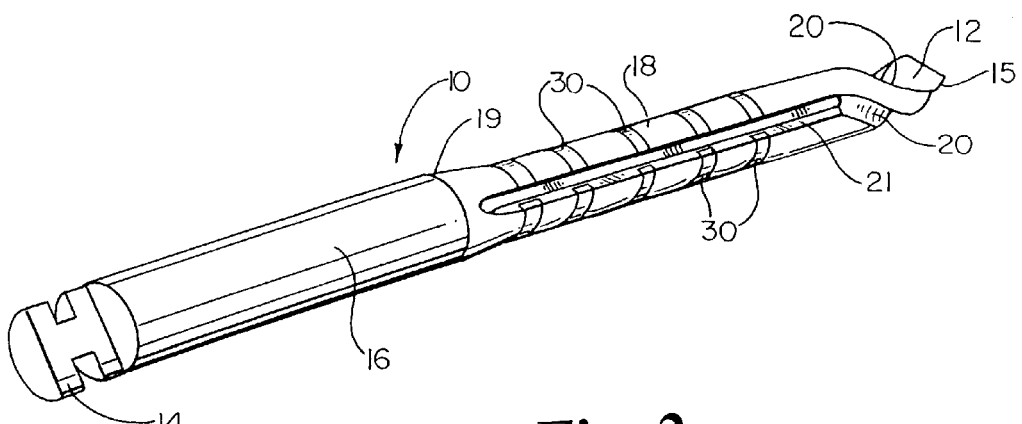
FIG. 1 is an isometric view of a finished drill in accordance with the present invention.
Figure 2:
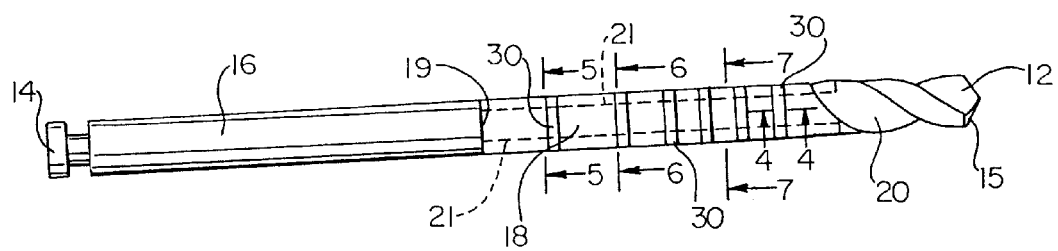
FIG. 2 is a side elevational view of a finished drill in accordance with the present invention.
Figure 3:
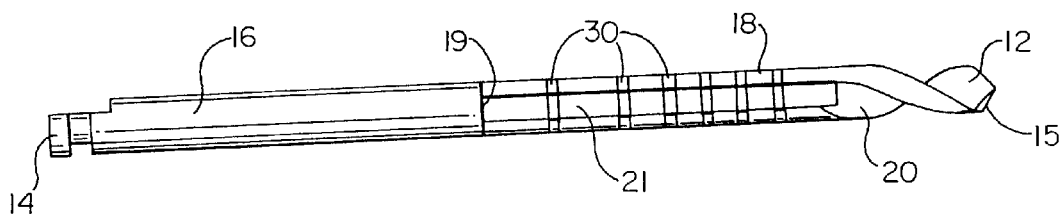
FIG. 3 is a side elevational view of a finished drill similar to that of FIG. 2, but with the drill rotated 90° about its longitudinal axis.

Reference is first made to FIGS. 1, 2 and 3 illustrating various views of a finished dental implant drill 10 in accordance with the present invention. As shown, the drill 10 includes an elongated, generally cylindrical configuration comprising an elongated shaft with a longitudinal axis. One end includes a cutting end 12, while the opposite end includes a connection or attachment end 14 for connection with a dental hand piece or the like (not shown).

The generally cylindrical drill includes an upper cylindrical shank portion 16 adjacent to the connection end 14 and a lower, generally cylindrical drill portion 18 adjacent to the cutting end 12. The cutting end 12 includes a cutting tip or cutting edge 15 as is conventional in the art. The drill portion 18 is designed to drill a hole in a tooth bone of a specified size in preparation for installation of a dental implant. Accordingly, the portion 10 has a diametrical dimension corresponding to the desired hole size. The drill shank portion 18 is integrally joined with the drill portion 16 at the shoulder 19.

Preferably the diameter of the shank portion 16 remains constant, regardless of the size of the drill portion 18. Thus, is some cases the diameter of the drill portion 18 is greater than that of the shank 16, while in other cases it is less. In the preferred embodiment as illustrated, the size of the drill portion 18 is 2.25 mm which is slightly less than the preferred diameter of the shank portion 16. Other conventional sizes of dental implant drills are 3.00 mm and 4.25 mm.

The cutting end 12 of the drill portion 18 can be comprised of any conventional drill cutting end known in the art such as spade drill or twist drill cutting ends, or the like. The cutting end 12 as shown in the preferred embodiment is that of a twist drill having a cutting tip or edge 15 and a pair of spiral flute portions 20 extending spirally upwardly and away from the cutting end 12 along the drill body. In a conventional twist drill, the spiral flutes extend along the entire length of the drill portion for the purpose of removing bone chips and other debris away from the cutting tip.

In accordance with the present invention, however, the lower end of the drill portion 18 is provided with a pair of spiral flute portions 20 extending from the cutting end 12 and joining with a pair of generally vertical or axially oriented flutes 21. The lower end of the flutes 21 are in communication with the spiral flute portions 20, while the upper ends of the flutes 21 extend above the intended drilling depth of the drill and toward the attachment end. Both the spiral flute portions 20 and the pair of axial flutes 21 are essentially channels in the surface of the drill portion 18 to assist in drawing and removing bone chips and debris away from the cutting tip during the drilling operation. As illustrated, the pair of axial flutes 21 are positioned on opposite sides of the drill portion 18 and extend along the drill portion 18 in a direction generally parallel to the longitudinal axis of the drill 10.

Figure 5:
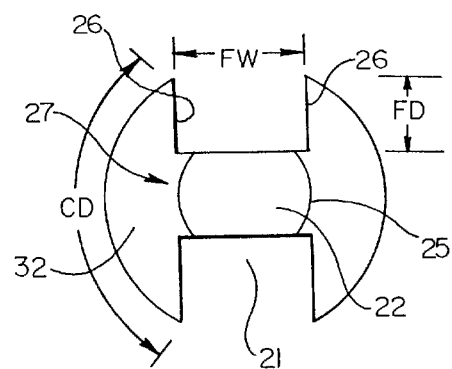
FIG. 5 is a view, partially in section, as viewed along the section line 5—5 of FIG. 2.
Figure 6:
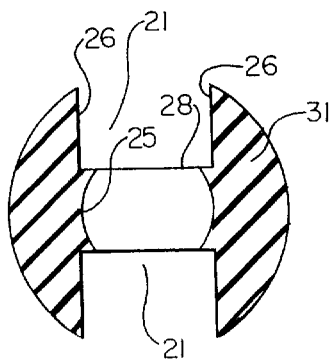
FIG. 6 is a view, partially in section, as viewed along the section line 6—6 of FIG. 2.
Figure 7:
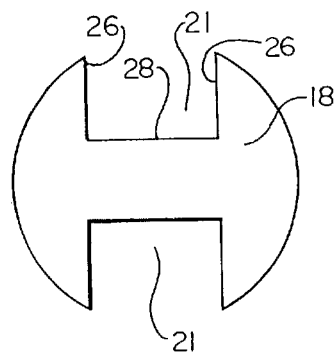
FIG. 7 is a view, partially in section, as viewed along the section line 7—7 of FIG. 2.

As shown best in FIGS. 5, 6 and 7, and particularly in FIG. 5, the cross-sectional configuration of the flutes 21,21 is defined by a flute width "FW" dimension and a flute depth "FD" dimension. These dimensions "FW" and "FD" are selected so that the size of the flute is sufficiently large to efficiently remove bone chips and other debris from the cutting tip during a drilling operation, yet small enough to provide sufficient bit strength in the center area 22 of the drill as well as sufficient circumferential distance "CD" of the surface portions 24,24 to provide acceptable visibility of the drill depth markings as the drill rotates. As shown in FIG. 5, the circumferential distance "CD" of the surface portions 24,24 is defined by the circumferential distances existing between adjacent edges of the axial flutes 21,21. In general, it is preferable for the circumferential distance of the portions 24,24 to comprise at least about 40%, more preferably at least about 50%, and most preferably at least about 60% of the total circumference of the drill portion 18. The dimensions "FW" and "FD" will vary with the size of the drill since a flute of larger cross-section will normally be needed for a larger drill size. In the preferred embodiment, the drill 10 is constructed of stainless steel, however, it is intended that the drill can be constructed of any of a variety of other materials from which medical or dental drills are commonly constructed.

Positioned along the length of the drill portion 18 are a plurality of depth indication bands 30. Each of these bands 30 is positioned at a specified location to define a specific distance between the cutting end 12 and such band to define a particular hole depth for a selected dental implant. Each of the bands 30 is preferably of a contrasting color so that the various hole depths are color coded and are also of a color distinguishable from the color of the shaft. Although all bands do not need to be of contrasting colors, at least adjacent bands 30 are preferably of contrasting colors. In the preferred embodiment, the bands are brightly colored bands formed of a colorant material. The colored bands 30 not only significantly improve the visibility of the depth markings, but also enable the drill operator to quickly and easily visually distinguish between the markings for different depths.

Figure 4:
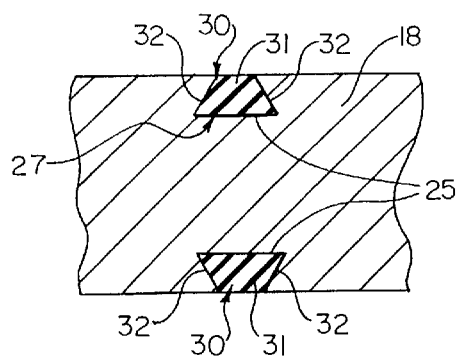
FIG. 4 is a view, partially in section, as viewed along the section line 4—4 of FIG. 2.

As illustrated best in FIGS. 4 and 5, the preferred structure of each of the depth indicating bands 30 is comprised of a circumferential groove or groove portion 27 and a color material 31 provided in the groove which is of a different color than the material from which the drill is constructed. Each groove 27 is defined by an inner circumferential surface 25 and a pair of side surfaces 32, 32 extending around the drill. The ends of the band portions terminate at the sides 26,26 of the axial flute 21. Preferably the outermost edge of the band portions approximates the outer diameter of the drill, however, this is not a necessity.

As shown best in FIG. 4, the side edges 32,32 of the groove are shown as having a negative draft. In other words, they slope away from each other toward the interior of the drill. This provides a means for retaining the color material 31 within the groove 27. Other means can be used to retain the color material 31 within the groove, include providing the surface with grit blasting, providing holes and corresponding pins, and various adhesives and other mechanical retaining means.

The drill bit in its finished form at any one point includes flute areas where the flute is present and non-flute areas where the flute is not present. Preferably, the groove or groove portions 27 are present only in the non-flute areas and preferably and the colored material is present only in the grooves 27 or non-flute areas and the flute areas are substantially free of any colored material or colored layer.

It is contemplated that the material 31 can comprise a variety of color materials. The color material 31 must, however, be sufficient to provide contrasting colors between adjacent bands 30 and have sufficient adhesive and hardness qualities to enable the color material to be retained within the groove and to prevent it from wearing away during the drilling process. It is also contemplated in accordance with the present invention that the color material 31 can be applied to the grooves in a variety of ways. In the preferred embodiment, the color material is applied into the grooves by injection molding techniques. During such injection molding process, mold surfaces are provided to define a mold cavity extending from the interior surface 25 to the exterior surface of the drill portion and from one edge 26 of the axial flute 21 to the adjacent edge 26 of the opposite flute 21. Preferably, the color material 31 is a polysulfone currently sold by Amoco Polymers, Inc. under the designation UDEL P-1700, with added colorant.

Although the preferred embodiment shows a plurality of grooves 30, the broadest aspect of the present invention does not require them. In the broadest form, the present invention includes a plurality of depth indicating contrasting colored bands, whether formed in grooves or not. These bands are provided on the working portion of the bit, (i.e.) that portion that is expected to extend into the drilled hole at some time during a drilling process. The present invention contemplates that the colored bands could be provided by means other than the grooves, such as by laser etching or some other process to color the drill bit in the working area.

The medical drill of the present invention can, if desired, incorporate various other medical drill features including, among possible others, an internal, axially extending hole for internal fluid irrigation. Such features, however, are not required structure to practice the present invention.

FIGS. 8, 9, 10 and 11 illustrate various intermediate structures of the drill of the present invention during the manufacturing process. Accordingly, these figures illustrate, in part, the method aspect of the present invention.

Figure 8:
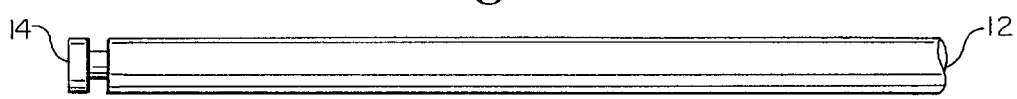
FIG. 8 is a plan view of a drill blank used to construct the drill of the present invention.
Figure 9:
FIGS. 9, 10 and 11 are partially machined drill blanks showing the construction stages of the drill of the present invention.

FIG. 8 illustrates a drill blank constructed of stainless steel and provided with a connection end 14 for connection with a hand piece or the like. The next step in the manufacturing process involves the machining operations illustrated in FIGS. 9, 10 and 11. Specifically, as shown in FIG. 9, a first machining operation forms the drill portion 18 to the desired drill diameter. The machining operation of FIG. 9 is for diameters the same size or smaller than the shank portion 16 of the drill. For drill diameters greater than the shank end, a larger drill blank is provided and the shank is machined down to the desired size.

Figure 10:
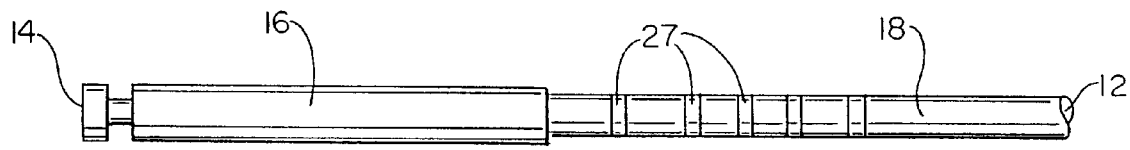
Figure 11:
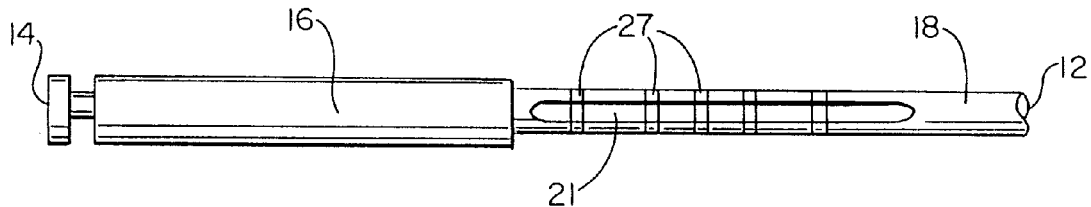

Next, as shown in FIG. 10, a plurality of grooves 27 are formed in the drill portion 18 at specified locations. Next, the pair of axial flutes 21 are machined longitudinally into the drill portion 18 as shown in FIG. 11. The order of the machining steps illustrated in FIGS. 10 and 11 is not critical. As shown, the grooves 27 and the flutes 21 intersect with one another. The grooves 27 are then filled with the colorant material 31. Any means can be used for this purpose; however, as indicated above, an injection molding process is preferred. Finally, the lower end of the drill portion 18 is machined to form the cutting end 12, the cutting tip 15 and the spiral flute portions 20, 20 as shown in FIGS. 1, 2 and 3. Again, there is no particular criticality in the order in which these steps are performed.

Figure 12:
FIGS. 12 and 13 are illustrations showing various groove constructions and filling material.
Figure 13:

The preferred embodiment shows the groove 27 as having sides 32, 32 with a negative draft so that the sides diverge from one another toward the axial center of the drill. It is contemplated, however, that these grooves could have a different configuration such as those illustrated in FIGS. 12 and 13.

Although the description of the preferred embodiment has been quite specific, it is contemplated that various modifications could be made without deviating from the spirit of the present invention. It is intended that all such modifications be covered by this disclosure. Accordingly, it is intended that the scope of the present invention be dictated by the appended claims rather than by the description of the preferred embodiment.

I claim:

1. A medical drill bit comprising:

an elongated shaft having a longitudinal axis, a cutting end at one of its ends and a rotation attachment end at its opposite end, said shaft further including a flute area extending from near its cutting end toward said rotation attachment end and a non-flute area extending from near its cutting end toward said rotation attachment end;

a plurality of depth indicating colored bands extending circumferentially around said elongated shaft in said non-flute area between said cutting end and said rotation attachment end, said colored bands being distinguishable from the color of said elongated shaft and at least two adjacent bands of said plurality of bands being of contrasting colors.

2. The medical drill of claim 1 wherein said flute area is a material removal flute extending from said cutting end toward said rotation end.

3. The medical drill bit of claim 2 wherein said material removal flute includes an axial flute portion extending along said elongated shaft generally parallel to said longitudinal axis.

4. The medical drill bit of claim 3 including a pair of axial flute portions being generally parallel to one another, generally parallel to said longitudinal axis and positioned on opposite sides of said elongated shaft.

5. The medical drill bit of claim 3 wherein said cutting end is a twist drill end.

6. The medical drill bit of claim 5 wherein said material removal flute includes a spiral flute portion extending from said cutting end and joining with said axial flute portion.

7. The medical drill bit of claim 1 wherein each of said plurality of colored bands includes a circumferentially extending groove in said non-flute area.

8. The medical drill bit of claim 7 wherein each of said grooves includes a colored surface.

9. The medical drill bit of claim 7 wherein each of said grooves includes a colored material.

10. The medical drill bit of claim 9 including means for retaining said colored material in said grooves.

11. The medical drill bit of claim 9 wherein said colored material substantially fills said grooves.

12. The medical drill bit of claim 9 wherein said flute area is substantially free of any colored material.

13. The medical drill bit of claim 1 being a dental drill bit.

14. The medical drill bit of claim 1 wherein said non-flute area comprises at least 50% of the total circumference of said elongated shaft.

15. A medical drill bit comprising:

an elongated shaft having a cutting end and an attachment end;

a material removal flute extending from said cutting end toward said attachment end wherein said elongated shaft includes a flute area where said material removal flute is present and a non-flute area where said material removal flute is not present; and at least one depth indicating colored band extending circumferentially around a portion of said elongated shaft, said colored band including a circumferentially extending groove in said non-flute area and a color material in said groove.

16. The medical drill bit of claim 15 wherein said flute area is free of any color material.

17. The medical drill bit of claim 15 wherein said non-flute portion comprises at least 50% of the total circumference of said elongated shaft.

18. The medical drill bit of claim 15 being a dental drill bit.

19. A method of making a medical drill bit comprising the steps of:

forming an elongated shaft with a cutting end and an attachment end;

cutting at least one circumferential groove in said elongated shaft;

cutting an axial flute portion in said elongated shaft so that it intersects with said at least one circumferential groove; and filling at least a portion of said groove with colorant material.

20. The method of claim 19 including cutting a plurality of circumferential grooves in said elongated shaft.

* * * * *